United States Patent
Kopansky et al.

(10) Patent No.: US 11,313,779 B2
(45) Date of Patent: Apr. 26, 2022

(54) LIQUID DEBRIS SENSOR AND SYSTEM

(71) Applicant: Eaton Intelligent Power Limited, Dublin (IE)

(72) Inventors: Gregory Kopansky, Philadelphia, PA (US); George P. Birch, Turnersville, NJ (US); Xin Pu, Chester Springs, PA (US); John Zielinski, Southampton, PA (US)

(73) Assignee: Eaton Intelligent Power Limited, Dublin (IE)

( * ) Notice: Subject to any disclaimer, the term of this patent is extended or adjusted under 35 U.S.C. 154(b) by 0 days.

(21) Appl. No.: 16/829,318

(22) Filed: Mar. 25, 2020

(65) Prior Publication Data

US 2020/0309662 A1  Oct. 1, 2020

Related U.S. Application Data

(60) Provisional application No. 62/823,929, filed on Mar. 26, 2019.

(51) Int. Cl.
*G01N 15/02* (2006.01)
*G01F 1/661* (2022.01)
*G01V 8/24* (2006.01)

(52) U.S. Cl.
CPC ......... *G01N 15/0205* (2013.01); *G01F 1/661* (2013.01); *G01V 8/24* (2013.01)

(58) Field of Classification Search
CPC ....... G01N 15/0205; G01F 1/661; G01V 8/24
USPC ....................... 356/335, 338, 342
See application file for complete search history.

(56) References Cited

U.S. PATENT DOCUMENTS

| | | | |
|---|---|---|---|
| 5,028,790 A | | 7/1991 | McGowan et al. |
| 5,131,741 A | * | 7/1992 | Zweben ............. G01P 3/36 356/28 |
| 5,241,368 A | * | 8/1993 | Ponstingl .......... G01N 21/8507 250/573 |
| 5,526,112 A | * | 6/1996 | Sahagen ............. A61B 5/0084 250/227.11 |
| 5,616,923 A | * | 4/1997 | Rich ................. G01N 21/0303 250/338.5 |
| 5,675,249 A | * | 10/1997 | LaClair ................. G01N 1/34 250/227.17 |

(Continued)

FOREIGN PATENT DOCUMENTS

CN  101718670 B  5/2011
CN  102393372 A  3/2012

(Continued)

OTHER PUBLICATIONS

European Search Report EP20165715, dated Jul. 7, 2020.
European Office Action, 20165715.2, dated Feb. 4, 2022.

*Primary Examiner* — Roy M Punnoose
(74) *Attorney, Agent, or Firm* — Fishman Stewart PLLC

(57) ABSTRACT

A debris detection system includes a chamber configured to permit particles to pass through the chamber; an optical fiber or fiber optic cable providing a light path; a collimator configured to channel light from the light path into the chamber; and a reflector configured to reflect light back to the collimator for signal detection. In embodiments, the reflector may include a mirror. Methods for detecting particles and information and/or parameters associated with particles, including that associated with reflected light, are disclosed.

20 Claims, 2 Drawing Sheets

(56) References Cited

U.S. PATENT DOCUMENTS

| | | | |
|---|---|---|---|
| 5,785,100 A | 7/1998 | Showalter et al. | |
| 5,831,730 A | 11/1998 | Traina et al. | |
| 6,315,955 B1* | 11/2001 | Klein | G01N 15/0211 |
| | | | 422/73 |
| 6,784,988 B2* | 8/2004 | Vijayakumar | G01N 15/0205 |
| | | | 250/574 |
| 7,173,706 B2* | 2/2007 | Wilson | G01N 21/3504 |
| | | | 356/432 |
| 7,382,458 B2* | 6/2008 | Johnson | G01N 21/8507 |
| | | | 356/136 |
| 10,352,865 B1* | 7/2019 | Yelvington | G01N 21/47 |
| 2005/0041125 A1 | 2/2005 | Kusuzawa | |
| 2010/0157304 A1* | 6/2010 | Takahashi | G01N 21/534 |
| | | | 356/442 |
| 2010/0201984 A1* | 8/2010 | Schuda | G01N 21/53 |
| | | | 356/338 |
| 2010/0235117 A1* | 9/2010 | Melnyk | G01P 5/26 |
| | | | 702/49 |
| 2017/0038299 A1* | 2/2017 | Long | G01N 21/6408 |
| 2018/0314107 A1 | 11/2018 | Park et al. | |
| 2019/0099082 A1* | 4/2019 | Jutte | G01N 33/497 |

FOREIGN PATENT DOCUMENTS

| | | |
|---|---|---|
| CN | 106168577 A | 11/2016 |
| CN | 107356541 A | 11/2017 |
| CN | 107884353 A | 4/2018 |
| JP | 2004/151445 A | 5/2004 |
| WO | 17/162804 A1 | 9/2017 |

\* cited by examiner

LIQUID DEBRIS SENSOR AND SYSTEM

RELATED APPLICATIONS

This application claims priority to U.S. Provisional Application No. 62/823,929, filed on Mar. 26, 2019, the contents of which are herein incorporated by reference in its entirety.

TECHNICAL FIELD

The present disclosure generally relates to debris (particle) detection systems, including liquid debris (particle) detection systems that may include a fiber optic sensor and which may be used to detect non-metals.

BACKGROUND

This background description is set forth below for the purpose of providing context only. Therefore, any aspect of this background description, to the extent that it does not otherwise qualify as prior art, is neither expressly nor impliedly admitted as prior art against the instant disclosure.

Debris monitoring systems can, for example, be used to detect the presence of wear particles in lubricating oils that may be transferred from the oil-wetted surfaces of gears and bearing under mechanical distress. Automatic debris monitoring is often preferred from a maintenance perspective, as it may eliminate the need for certain routine inspections and may preempt the potential failure should an issue advance faster than an inspection interval. With a number of applications the aerospace industry is trending towards "on-condition" maintenance—meaning the Line Replaceable Unit (LRU) should not require routine maintenance or inspections, and preferably will fail "soft" (i.e., the LRU will signal when it needs calibration or service, while maintaining some level of degraded operability).

There are two general classes of debris monitors: (1) capturing and (2) flow-through. Capturing sensors may, for example, employ a high-strength magnet to attract particles and detects particles via inductive principles. The particles can then be inspected and further tested to determine if they are representative of gear or bearing steel, or if they are nuisance debris. A potential challenge with capturing type sensors is that the build-up of particles may affect the accuracy of size discrimination and eventually the sensor could become "saturated" and unresponsive to additional particle captures, and may therefore require routine maintenance.

Flow-through debris monitors generally work on the principle of induction and may respond to both ferrous and non-ferrous debris. Since flow-through debris monitors do not capture particles they generally do not require routine maintenance. However, particle inspections are not necessarily a feature or capability.

Moreover, with the introduction of hybrid bearings (e.g., steel races with ceramic rolling elements), there is currently a need for the detection of non-metals in the aerospace industry.

That is, hybrid bearings are now in use in many industries. Hybrid bearing have many important features or qualities that can improve engine efficiencies. Among other things, employing hybrid bearings may provide lower weight, higher DN speeds (bearing diameter times operating speed), higher temperature operation, less dependence on lubrication, and lower centrifugal forces (due to lighter weight), which may permit their operation at higher speeds.

However, the deployment of hybrid bearings may, among other things, require a viable technology that may need to be approved for various applications (such as flight), and that can detect non-metals.

Consequently, there is a desire for solutions/options that address one or more of the aforementioned challenges. The foregoing discussion is intended only to illustrate examples of the present field and should not be taken as a disavowal of scope.

SUMMARY

A debris (particle) detection system includes a chamber configured to permit debris (particles) to pass through the chamber; an optical fiber providing a light path; a collimator configured to channel light from the light path into the chamber; and a reflector configured to reflect light back to the collimator for signal detection. In embodiments, the reflector may include a mirror. Methods for detecting particles and information and/or parameters associated with particles within the chamber via reflected light are disclosed, including, inter alia, methods for detecting particle size by measuring reflected light within the chamber light signal amplitude blocked by individual particulates.

The foregoing and other aspects, features, details, utilities, and/or advantages of embodiments of the present disclosure will be apparent from reading the following description, and from reviewing the accompanying drawings.

DETAILED DESCRIPTION

Reference will now be made in detail to embodiments of the present disclosure, examples of which are described herein and illustrated in the accompanying drawings. While the present disclosure will be described in conjunction with embodiments and/or examples, it will be understood that they are not intended to limit the present disclosure to these embodiments and/or examples. On the contrary, the present disclosure is intended to cover alternatives, modifications, and equivalents.

Figure 1:
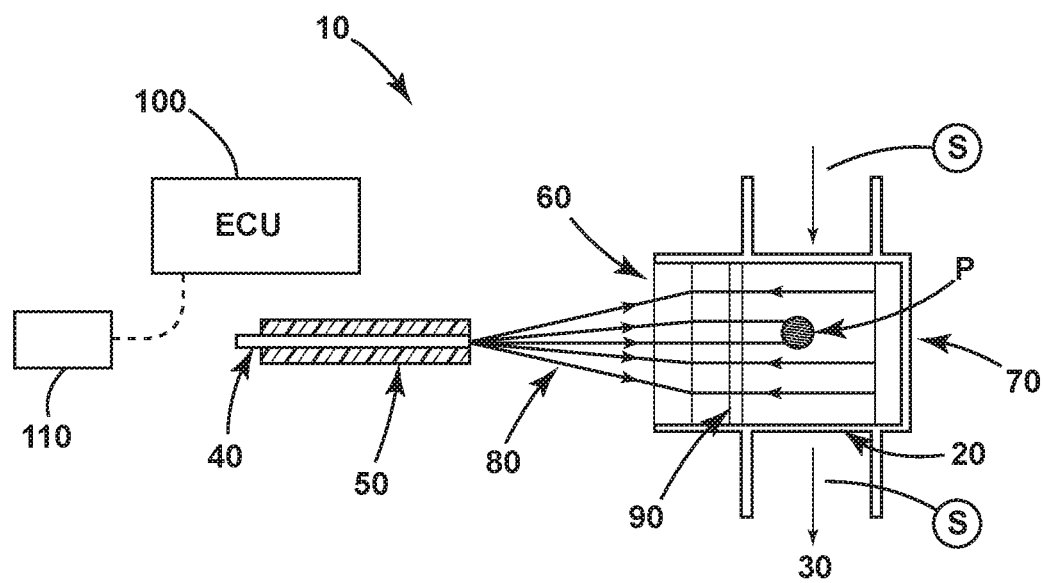
FIG. 1 is a top view that generally illustrates a detection system according to teachings of the present disclosure.

FIG. 1 generally illustrates a debris detection system (or debris detector) 10 embodying aspects/teachings of the present disclosure. Without limitation, such debris detection systems may be used in various mechanical-fluid configurations, such as a gearbox for various vehicles. As generally shown, a debris detection system 10 may include a chamber 20. The chamber 20 may be a flow-through chamber, and may be configured to permit the flow of fluid (fluid flow 30) through the chamber.

As generally illustrated, the system 10 may include an optical fiber 40 (which may or may not comprise a single fiber), which may be supported by a structure or structural member 50; a collimator 60; and a reflector 70. In embodiments, the optical fiber 40 may provide light and an associated light path 80; the reflector 70 may comprise one or more mirrors; and/or the collimator 60 may be configured to channel light from a light path 80 from the optical fiber 40 into the chamber 20. The reflector 70 may be configured to reflect light from the light path back to a collimator (or collimator lens) 60 for signal detection.

In embodiments, the system 10 may include an optical window 90 that may be flat or substantially planar and may be disposed within the chamber 20. The optical window 90 may be positioned between the collimator 60 and the reflector (e.g., mirror) 70. In contrast with some optical systems that may require a prism, embodiments of the present disclosure may be provided without a prism and/or may employ an optical window 90 that is flat.

As generally illustrated in connection with FIG. 1, a particle (or particulate) P of debris in the fluid flow 30 passing through the chamber 20 may (at least for a period of time) block a light path between the collimator 60 and the reflector 70 (e.g., mirror). For example, as generally illustrated in FIG. 1, for the instant that is depicted (i.e., a snapshot of the fluid flow), a particle P is shown blocking the light lines of the light path 80 that are shown contacting a portion of the particle P. In embodiments, debris size may be detected by the system, for example, by measuring the light reflected within the chamber 20 within the chamber light signal amplitude that is blocked by the particulate P. Because of the manner in which the system 10 functions, the existence of particles and attributes thereof (e.g., particle size) may be detected without regard to the particle's inherent material composition. Systems may, for example, be configured to correlate changes in light lost (e.g., light that is not returned from a reflector as having its path blocked by a particle P) with aspects or attributes associated with one or more particles.

In embodiments, the system 10 may include additional sensors. For example and without limitation, the system 10 may include one or more sensors S that detect/measure fluid flow at positions prior to and/or subsequent to the chamber. Such additional sensors S may be operatively connected (e.g., physically or wirelessly) to an ECU 100, including an ECU associated with the foregoing.

In embodiments, the system 10 may include an electronic control unit (ECU) 100, which may be in physical and/or operative connection or communication with one or more other components of the system 10. In embodiments, an ECU 100 may include an electronic controller and/or include an electronic processor, such as a programmable microprocessor and/or microcontroller. In embodiments, an ECU may include, for example, an application specific integrated circuit (ASIC). An ECU may include a central processing unit (CPU), a memory (e.g., a non-transitory computer-readable storage medium), and/or an input/output (I/O) interface. An ECU may be configured to perform various functions and/or analysis, and may include appropriate programming instructions and/or code embodied in software, hardware, and/or other medium. In embodiments, an ECU may include a plurality of controllers. In embodiments, an ECU may be connected (e.g., physically or wirelessly) to a visual display 110, such as a touchscreen display (which may, for example and without limitation, be in the form of a monitor, tablet, or mobile device). Moreover, embodiments of a system may be configured to assess the detected results, which may involve an assessment of particles in the flow, to monitor and/or identify the condition of the flow-through a chamber. For example and without limitation, an ECU may assess whether the flow is normal or abnormal (and even actionable, problematic, and/or dangerous) based on the assessment of parameters associated with particles monitored in connection with a system flow-through. In embodiments, the system may determine and/or evaluate information or parameters associated with one or more particles within the chamber, for example, particle size (e.g., particles that a bigger than a set or predetermined size parameter), flow-through rate (e.g., too many particles detected within a set or predetermined time frame), particle density (e.g., too many particles overlapping or in proximity to one another), or other parameters. While the system may utilize algorithms and/or various software to control the system and one or more various outputs or signals, simple analog configurations may also be utilized if/when appropriate. For example and without limitation, a system may be configured such that a mere change in a detected light intensity (at some set or predetermined threshold) that is associated with a particle (or its presence) may provide a yeah/nay (go-no go, 1 or 0) system response.

Figure 2:
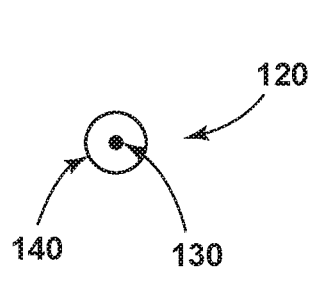
FIGS. 2 and 3 are cross-sectional views generally illustrating embodiments of a single fiber configuration and a multiple fiber configuration, respectively.

FIG. 2 generally illustrates an embodiment of a single fiber configuration, or single fiber optic cable 120. The single fiber configuration/cable 120 may include a single optical fiber 130 and a fiber supporting structure or structural member 140. In embodiments, the single optical fiber 130 may comprise an emitter/detector combination provided in connection with the single fiber.

Figure 3:
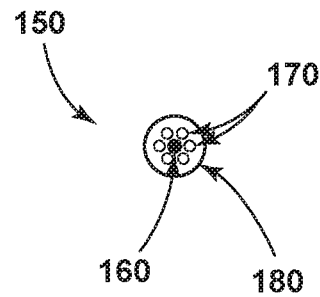

FIG. 3 generally illustrates an embodiment of a multiple fiber configuration, or multiple fiber cable 150. The multiple fiber optic configuration, or multiple fiber optic cable 150, may include a first optical fiber (e.g., light emitter) 160, a plurality of second optical fibers (e.g., light detectors) 170, and a fiber supporting structure (or structural member) 180. In embodiments, the first optical fiber 160 may comprise a central optical fiber that may be configured to be a light emitter, and the second optical fibers 170 may comprise light detectors and may be arranged or clustered about the first optical fiber 160 (e.g., in a planetary arrangement). The fiber supporting structure 180 may encase both a first optical fiber 160 and a plurality of second optical fibers 170.

With embodiments of systems 10, a single cable—whether having a single fiber (e.g., single fiber optic cable 120) or a multiple fibers (e.g., multiple fiber optic cable 150)—may be employed.

Embodiments of debris detection systems such as disclosed may provide various advantages. For example and without limitation, such systems: (a) may function in an "on-condition" mode and may be employed "in-line" or in an active/constant fluid stream; (b) may provide independence from debris material or composition (e.g., making it irrelevant if the particle or debris material is comprised of a metal or non-metal (such as, without limitation, a ceramic)); (c) may provide independence (e.g., inherent independence) from temperature; (d) may provide or permit high temperature functionality and capabilities; (e) may be used in conjunction with cyclonic (e.g., Lubriclone™) or other forms of separators (e.g., as a supplemental system); and/or may have a single fiber or multiple fiber configuration.

Figure 4:
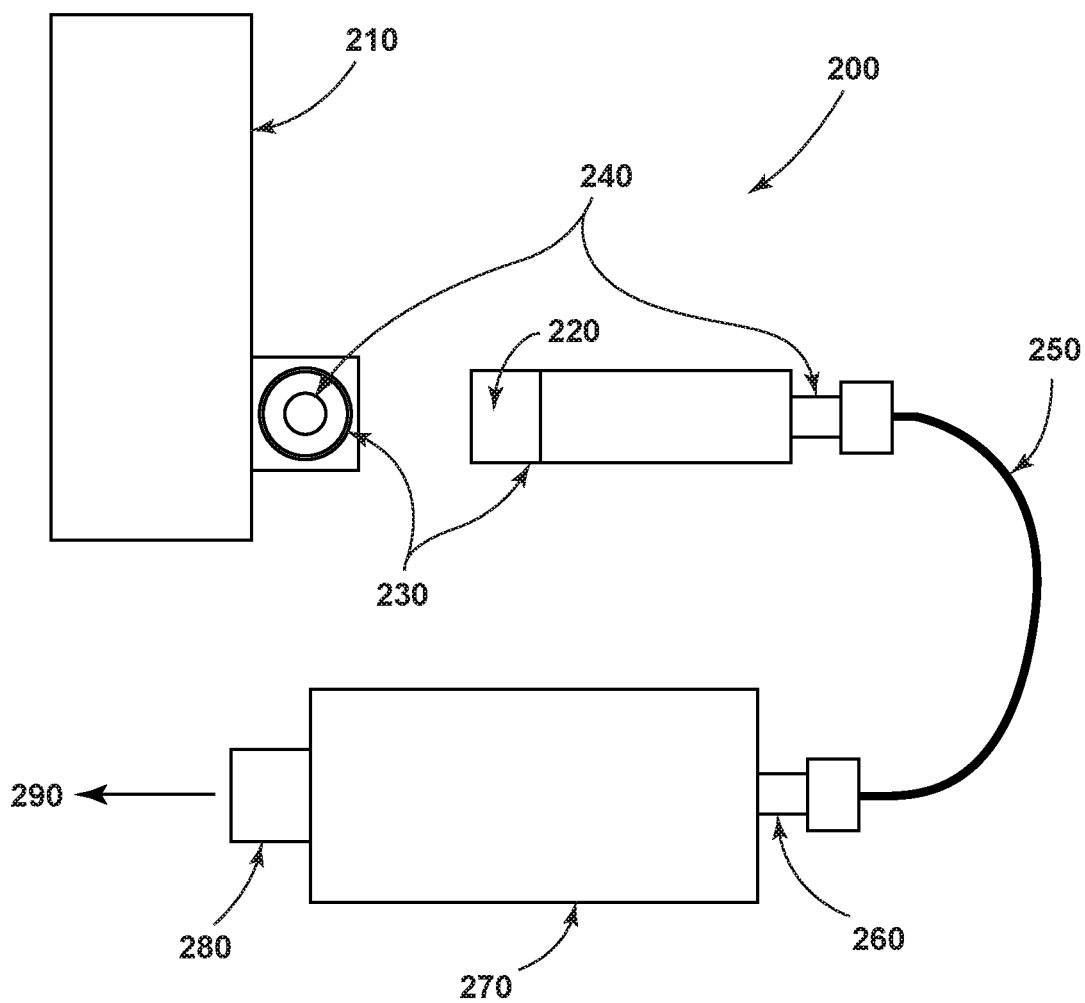
FIG. 4 is a representation of an embodiment of a cyclonic debris separator system configuration.

FIG. 4 is a representation of an embodiment of a cyclonic debris separator system 200 configuration in accordance with aspects or teachings of the present concept. An embodiment of such a system, as generally illustrated, may include a cyclonic debris separator 210, a debris chamber 220, a sensor 230, a first fiber optic connector 240, a fiber optic cable 250, a second fiber optic connector 260, a signal conditioning unit 270, an electrical connector 280. The system may proceed further to an external interface 290, which may have various forms of interface.

Various embodiments are described herein for various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments.

Reference throughout the specification to "various embodiments," "with embodiments," "in embodiments," or "an embodiment," or the like, means that a particular feature, structure, or characteristic described in connection with the embodiment is included in at least one embodiment. Thus, appearances of the phrases "in various embodiments," "with embodiments," "in embodiments," or "an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment/example may be combined, in whole or in part, with the features, structures, functions, and/or characteristics of one or more other embodiments/examples without limitation given that such combination is not illogical or non-functional. Moreover, many modifications may be made to adapt a particular situation or material to the teachings of the present disclosure without departing from the scope thereof.

It should be understood that references to a single element are not necessarily so limited and may include one or more of such element. Any directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of embodiments.

Joinder references (e.g., attached, coupled, connected, and the like) are to be construed broadly and may include intermediate members between a connection of elements and relative movement between elements. As such, joinder references do not necessarily imply that two elements are directly connected/coupled and in fixed relation to each other. The use of "e.g." in the specification is to be construed broadly and is used to provide non-limiting examples of embodiments of the disclosure, and the disclosure is not limited to such examples. Uses of and "or" are to be construed broadly (e.g., to be treated as "and/or"). For example and without limitation, uses of "and" do not necessarily require all elements or features listed, and uses of "or" are intended to be inclusive unless such a construction would be illogical.

While processes, systems, and methods may be described herein in connection with one or more steps in a particular sequence, it should be understood that such methods may be practiced with the steps in a different order, with certain steps performed simultaneously, with additional steps, and/or with certain described steps omitted.

It is intended that all matter contained in the above description or shown in the accompanying drawings shall be interpreted as illustrative only and not limiting. Changes in detail or structure may be made without departing from the present disclosure.

What is claimed is:

1. A debris detection system, comprising:
   a chamber configured to permit fluid flow to pass through the chamber;
   a fiber optic cable providing a light path;
   a collimator, the collimator configured to channel light from the light path into the chamber;
   a reflector, the reflector configured to reflect light channeled into the chamber from the light path back to the collimator for signal detection; and
   an electronic control unit (ECU), the ECU configured to detect the existence of debris particles in the fluid flow path based on the detection of blockage of the light path between the collimator and the reflector, and wherein the detection is without regard to inherent material composition of the detected debris particles.

2. The system of claim 1, wherein the reflector comprises a mirror.

3. The system of claim 1, including an optical window disposed in the chamber and positioned between the collimator and the reflector.

4. The system of claim 3, wherein the optical window is flat or substantially planar.

5. The system of claim 1, wherein the fiber optic cable includes a structural member.

6. The system of claim 1, wherein the fiber optic cable comprises a single optical fiber.

7. The system of claim 1, wherein the fiber optic cable includes a plurality of optical fibers.

8. The system of claim 1, wherein the fiber optic cable includes a first optical fiber and one or more second optical fibers.

9. The system of claim 1, wherein the fiber optic cable includes a first optical fiber and a plurality of second optical fibers, the first optical fiber configured to function as a light emitter and the second optical fibers configured to function as light detectors.

10. The system of claim 9, wherein the plurality of second optical fibers are arranged or clustered about the first optical fiber.

11. The system of claim 1, wherein the fluid flow through the chamber includes a particle of debris, and the particle of debris blocks light from reaching the reflector.

12. The system of claim 1, wherein the electronic control unit (ECU) is configured to access the fluid flow, based on detected debris particles in the fluid flow and identify the condition of the fluid flow through the system.

13. The system of claim 1, including one or more sensors configured to detect/measure fluid flow.

14. The system of claim 13, wherein the one or more sensors detect/measure fluid flow at positions prior to and/or subsequent to the chamber.

15. The system of claim 13, wherein the one or more sensors are operatively connected to an electronic control unit (ECU).

16. The system of claim 1, including a visual display connected physically or wirelessly to the ECU.

17. The system of claim 1, wherein the ECU determines and/or evaluates information or parameters associated with one or more particles within the chamber.

18. The system of claim 17, wherein the ECU determines and/or evaluates the presence of particles of a set or predetermined size.

19. A method for detecting information or parameters associated with particles in a fluid flow using a debris detection system including the steps of:
  permitting fluid flow to pass through a chamber;
  providing a light path;
  using a collimator to channel light from the light path into the chamber;
  reflecting the light channeled into the chamber from the light path back to the collimator for signal detection; and
  using an electronic control unit (ECU) to detect debris particles in the fluid flow path that block the light path between the collimator and the reflector, wherein the ECU is configured to detect blocked light from the collimator that is associated the blockage of the light path caused by debris particles in the fluid flow path, and the detection is without regard to inherent material composition of the detected debris particles.

20. The method of claim 19, further including the step of evaluating the reflected light within the chamber blocked by one or more particles.

* * * * *